United States Patent [19]
Komatsu et al.

[11] Patent Number: 6,008,401
[45] Date of Patent: Dec. 28, 1999

[54] PROCESS FOR PRODUCING AN OPTICALLY ACTIVE COMPOUND

[75] Inventors: Shin-ichi Komatsu; Akira Takagi; Yoshihiro Kobori, all of Yokohama, Japan

[73] Assignee: Nippon Oil Co., Ltd., Tokyo, Japan

[21] Appl. No.: 09/026,428

[22] Filed: Feb. 19, 1998

[30] Foreign Application Priority Data

Feb. 21, 1997 [JP] Japan .................................. 9-052548

[51] Int. Cl.$^6$ ......................... C07C 455/00; C07C 63/00
[52] U.S. Cl. ........................................... 558/423; 562/405
[58] Field of Search ............................... 558/423; 562/465

[56] References Cited

PUBLICATIONS

Org Syn Col vol. 4, 93, 1963.
Org Syn Col vol. 5, 926, 1973.
Meek et al, JACS, 78, 5413, 1956.
Russell A. Lewthwaite, John W. Goodby and Kenneth J. Toyne; The effect of a lateral hydroxy substituent on the thermal stability of the chiral smectic C phase; Liquid Crystals, 1994, vol. 16, No. 2, pp. 299–313.

*Primary Examiner*—Johann Richter
*Assistant Examiner*—Joseph Murray
*Attorney, Agent, or Firm*—Akin, Gump, Strauss, Hauer & Feld, L.L.P.

[57] ABSTRACT

A process is disclosed for producing an optical active alkoxybenzonitrile derivative in which process a benzonitrile derivative is subjected to condensation reaction with an optical active alcohol.

A process is also disclosed for producing an optical active alkoxy benzoic acid derivative in which process a benzonitrile derivative is subjected to condensation reaction with an optical active alcohol and the reaction product thus derived is hydrolyzed.

In these processes conversion of an optical active alcohol to tosylate or halide is not required and thus it is possible to produces producing an optical active alkoxybenzonitrile derivative and an optical active alkoxy benzoic acid derivative in a simple and inexpensive manner.

8 Claims, No Drawings

PROCESS FOR PRODUCING AN OPTICALLY ACTIVE COMPOUND

BACKGROUND OF THE INVENTION

1. Field of the Invention

This invention relates to a process for the production of optical active alkoxybenzonitrile derivatives and optical active alkoxybenzoic acid derivatives which have utility as medicines, materials for liquid crystal or intermediates thereof.

2. Prior Art

It has been known that an optical active alkoxybenzonitrile having an optical active alkoxy group bonded through an oxygen atom to benzonitrile at the 4 position finds extensive use for materials of liquid crystal and medicines. However, there has not been developed a method for synthesizing such optical active compounds which can be utilized universally in a simple manner.

Williamson Method is known for synthesis of compounds having ether bonds as well as alkoxybenzonitrile in which method alkoxide is reacted with alkylhalide or alkyltosylate. However, the synthesis of an optical active alkoxybenzonitrile using this method accompanies a problem that an optical active alkylhalide and alkyltosylate used as a starting material can not be mass-produce in an inexpensive manner and particularly the former is susceptible to reduced optical purity. Furthermore, this synthesis method involves another problem that if an optical active secondary alkylhalide or alkyltosylate is used as a starting material the resulting compound is attached with a risk of reduction in optical purity depending upon kinds of the secondary alkyl groups and the reaction conditions because the reaction of Williamson method progresses in $S_N2$ reaction system and in this connection the asymmetric center becomes the reaction center.

On the other hand, Williamson Method is employed also for synthesizing an optical active alkoxy benzoic acid having an alkyl group bonding through an oxygen atom to the 4-position of benzoic acid by reacting 4-hydroxybenzoic acid or the ester thereof and an optical active alkylhalide or alkyltosylate under basic conditions. For instance, in a publication entitled "Liquid Crystals" 16.299 (1994), there is reported a method for synthesizing an optical active alkoxy benzoic acid by reacting tosylate derived from a variety of optical active secondary alcohol with methyl 4-hydroxy benzoic acid and hydrolyzing the resulting methyl alkoxybenzoate. However, the products derived from the method also encounter reduction of optical purity and involve with a problem that the preparation of an optical active alkyltosylate used as a starting material requires much expenditure.

SUMMARY OF THE INVENTION

It is therefore an object of the present invention to solve the foregoing problems arising upon synthesis of an alkoxybenzonitrile or alkoxy benzoic acid in accordance with Williamson Method.

More specifically, the present invention seeks to provide a process for producing an optical alkoxybenzonitrile or alkoxybenzoic acid using an optical active alcohol which is easily available in industrial view with no reduction in optical purity occurred during the process, without employing Williamson Method which invites the reduction of optical purity and incurs expense in the preparation of the starting material.

It has now been found after extensive research that an optical active alkoxy benzoic acid derivative can be produced by hydrolyzing an optical active alkoxybenzonitrile derivative derived from condensation reaction of an optical alcohol and an optical benzonitrile derivative to condensation reaction under basic conditions.

According to the invention, there is provided a process for producing an optical active alkoxybenzonitrile derivative by condensation reaction of a benzonitrile derivative and an optical active alcohol under basic conditions.

The term "optical active alkoxybenzonitrile derivative" used herein designates a compound having an optical active alkyl group bonding through an oxygen group to the 4-position of each of one or two molecules of benzonitrile and such compounds are encompassed by 4-optical active alkyloxybenzonitrile and 4,4'-optical active alkyldioxybis-benzonitrile.

The present invention is characterized by direct use of an optical active alcohol as a starting material. The inventive method is thus in extreme contrast with Williamson Method in which an optical active alkylhalide or alkyltosylate is necessarily prepared from an optical alcohol.

In the case of using menthol as an optical active alcohol, the optical active alkoxybenzonitrile derivative derived from the inventive process is different in configuration from that produced from the tosylated product from menthol in accordance with Williamson Method.

A benzonitrile derivative used as a starting material in the inventive process is represented by the formula

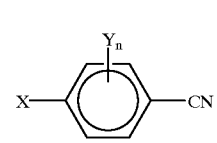

(I)

wherein X is a fluorine or chlorine atom or a nitro group, Y is a $C_1$–$C_{10}$ alkyl group and n is an integer of 1–4.

Preferred compounds represented by formula (I) are 4-fluorobenzonitrile, 4-chlorobenzonitrile, 4-nitrobenzonitrile and these may be used in combination.

Eligible optical active alcohols for the inventive process are a $C_4$–$C_{30}$, preferably $C_4$–$C_{20}$, more preferably $C_4$–$C_{10}$ monoalcohol, a $C_3$–$C_{30}$, preferably $C_3$–$C_{20}$, more preferably $C_3$–$C_{10}$ diol and a $C_4$–$C_{30}$, preferably $C_4$–$C_{20}$, more preferably $C_4$–$C_{10}$ triol. In general, these alcohols are primary or secondary alcohols but tertiary alcohols are also eligible.

Alternatively, by using diol or triol having the tertiary carbon atom bonded to a hydroxyl group, an optical active alkoxybenzonitrile derivative having the said tertiary carbon atom can be synthesized.

Specific examples of monoalcohols eligible for the inventive process are 2-butanol, 2-pentanol, 2-hexanol, 2-heptanol, 2-octanol, 2-nonanol, 2-decanol, 2-undecanol, 2-dodecanol, 3-hexanol, 3-heptanol, 3-octanol, 3-nonanol, 3-decanol, 3-undecanol, 3-dodecanol, 2-methylbutanol, 2-methylpentanol, 2-methylhexanol, 2-methylheptanol, 2-methyloctanol, 3-methylpentanol, 3-methylhexanol, 3-methylheptanol, 3-methyloctanol, 4-methylhexanol, 4-methylheptanol, 4-methyloctanol, 2-methylcyclohexanol, 3-methylcyclohexanol, norbornane-2-ol, borneol, menthol and isomenthol.

Eligible diols are propane-1,2-diol, butane-1,2-diol, butane-1,3-diol, butane-2,3-diol, pentane-1,2-diol, pentane-1,3-diol, pentane-1,3-diol, pentane-1,4-diol, pentane-2,4- diol, cyclohexane-1,2-diol, 2-methylbutane-1,4-diol, and norbornane-2,3-diol while eligible triol is butane-1,2,4-triol.

Upon reaction of a benzonitrile derivative of formula (I) and an optical active alcohol, monoalcohol is used in an amount of 0.5–2, preferably 0.7–1.3 mol per mol of the benzonotrile derivative. Diol or triol is used in half or one third of the amount specified with respect to monoalcohol.

The reaction of a benzonitrile derivative of formula (I) and an optical active alcohol means that a reaction between fluorine, chlorine or nitro group bonded to the 4-position of benzonitrile and hydroxyl group of the optical active alcohol. Therefore, in consideration given to stoichiometry, in order to produce 4-optical active alkyloxybenzonitrile in accordance with the inventive process, an optical active monoalcohol needs to be used in an amount of one mol per mol of a benzonitrile derivative of formula (I) whereas in order to produce 4,4'-optical active alkyldioxybisbenzonitrile, an optical active diol needs to be used in an amount of half mol per mol of a benzonitrile of formula (I). The use of an optical active alcohol in an amount exceeding stoichiometric amount is not recommendable in view of economic reason. However, if 4,4'-optical active alkyldioxybisbenzonitrile is intended to be synthesized, an optical active diol should be used in amount of 70–100, preferably 90–100 percent of the stoichiometric amount to suppress the by-production of 4-optical active alkyoxybenzonitrile.

Upon reaction of a benzonitrile of formula (I) and an optical active alcohol, there may be used an organic or inorganic base.

Specific examples of the base used in the reaction are tertiary amines such as triethylamines, pyridine, picoline, quinoline and isoquinoline, alkali metal alcoholates such as potassium t-butylato, alkali earth metal or alkali metals such as metal lithium, metal potassium and metal calcium, alkali metal hydroxides such as lithium hydroxide, sodium hydroxide, potassium hydroxide and calcium hydroxide or alkali earth metal hydroxides, alkali metal hydrides such as lithium hydride, sodium hydride and potassium hydride and alkyl lithiums such as butyl lithium, phenyl lithium and methyl lithium. These bases may be used in combination.

Preferred bases are sodium hydride, metal sodium and potassium t-butylato among which sodium hydride is particularly preferred.

The base is used in an amount of 0.9–100, preferably 1–10 mols per mol of the alcohol in the case of using monoalcohol and used in the range of half to one third of the amount specified with respect to the monoalcohol in the case of using diol or triol.

Upon condensation reaction of the invention, there may be used a reactive solvent which is exemplified by the above-mentioned tartiary amines, amides such as dimethylformaldehyde and dimethylacetamide, sulfoxides such as dimethylsulfoxide and sulfolane and ethers such as tetrahydrofuran, dioxane and diglyme among which dimethylformaldehyde, dimethylacetamide and tetrahydofuran are preferred and dimethylformaldehyde is particularly preferred.

The amount of the reactive solvent is selected arbitrarily as long as it can be mixed uniformly with a benzonitrile of formula (I), an optical active alcohol and a base by stirring. The reactive solvent is preferably used in an amount ranging from 1–100, preferably 2–10 grams per one gram of an optical active alcohol.

There is no restriction imposed upon the order of contact of a benzonitrile derivative of formula (I), an optical active alcohol and a base. Therefore, these components may be contacted in the following sequences.

(I) all components are mixed simultaneously.

(II) an optical active alcohol and a base are mixed and thereafter added with a benzonitrile derivative.

(III) a benzonitrile derivative and a base are mixed and thereafter added with an optical active alcohol.

(IV) a benzonitrile derivative and an optical active alcohol are mixed and thereafter added with a base.

However, if there is used a base such as lithium hydride, sodium hydride, potassium hydride, metal lithium, metal sodium and metal potassium, it is preferred to employ sequence (II) in which a base and an optical active alcohol are mixed to form alcholate and thereafter a benzonitrile derivative is added so as to avoid a risk such as bumping.

The reaction temperature for formation of alcholate is in the range of 0–100° C., preferably 10–50° C. while the reaction time for the same is in the range of 10 minutes to 48 hours, preferably 1–24 hours.

In any of sequence (I) through (IV) being employed, a benzonitrile derivative of formula (I) is reacted with an optical active alcohol or an optical active alkoxide at a temperature of −50–100° C., preferably −20–50° C. for 5 minutes to 48 hours, preferably 10 minutes to 24 hours thereby obtaining the intended optical active alkoxybenzonitrile derivative at high yield. The optical active alkoxybenzonitrile derivative thus obtained may be recovered of refined from the reaction mixture in a conventional method such as distillation, recrystallization, extraction and chromatography.

For instance, the intended reaction product can be recovered from the reaction mixture by distilling the reactive solvent. In this case, to suppress denaturation of the reaction product the base component may be inactivated by adding water, acetate, and diluted hydrochloric acid prior to distillation of the reaction mixture. However, the distillation of the solvent is not necessarily required and the intended product can be separated out by putting the reaction mixture into water in an amount of from 3 to 10 times greater than the volume of the reaction mixture. Although the precipitated reaction product can be recovered by filtration, there may be used an alternative that after extraction using an organic solvent such as ethyl acetate, ether, toluene, chloroform and methylene chloride and then removing water remaining in the organic solvent phase as needed, the reaction product can be recovered by distilling out the organic solvent.

Although the recovered reaction product remaining as it is may be put in use as a starting material of an optical active alkoxy benzoic acid derivative, a high purity optical active alkoxybenzonitrile derivative can be obtained by distilling the intended product which had been recrystallized using methanol, ethanol, isopropanol, acetrinitrile or dimethylformaldehyde or, refining the same by means of column chromatography.

In the following, an explanation is made on a process for producing an optical active alkoxy benzoic acid derivative.

The process according to the invention comprises the steps of (a) subjecting a benzonitrile of formula (I) and an optical active alcohol to condensation reaction in the presence of a base to obtain an optical active alkoxybenzonitrile derivative and (b) hydrolyzing the nitrile group of the derivative thus obtained to be converted to carboxyl group.

The reaction mixture obtained in step (a) as it is may be supplied to step (b). However, if using a reactive solvent in step (a), the reaction mixture is preferably supplied to step (b) after removing the solvent therefrom because the solvent used in step (a) is different from that used in step (b).

Hydrolyzation in step (b) may be conducted in a conventional method such as (i) by hydrolyzing the optical active alkoxybenzonitrile derivative so as to be an amide group in the presence of an acid or base compound and (ii) and then hydrolyzing the nitrile group of the optical active alkoxybenzonitrile derivative in the presence of hydrogen peroxide, followed by hydrolyzation of the amid group in the presence alkali or acid or in the presence of nitrite. Generally, the method (i) is preferred because of less procedure.

The basic material used in method (i) is preferably an alkali metal hydroxide such as sodium hydroxide, lithium hydroxide and potassium hydroxide. If sodium hydroxide lithium hydroxide or potassium hydroxide is used as a base in step (a), sodium hydride, metallic sodium or metallic potassium remaining in the reaction mixture may be reacted with water to derive an alkali metal hydroxide, which can be used as the basic material as needed in step (b).

The required amounts of the base material for hydrolyzation are varied depending on the number of nitrile group contained in per molecule of an optical active alkoxybenzonitrile derivative. The base material is used in an amount of 1 to 20, preferably 2 to 10 mols per mol of the derivative if one nitrile group is contained and in amount of 2 to 40, preferably 4 to 40 mols per mol of the derivative if two nitrile groups are contained. Upon hydrolyzation, water is generally used in an amount exceeding stoichiometric amount. In the case of hydrolyzing an optical active alkoxybenzonitrile having one nitrile group per molecule, water is used in an amount of 3 to 100, preferably 5 to 20 mols per mol of the derivative. In the case of hydrolyzing an optical active alkoxybenzonitrile having two nitrile groups per molecule, water is used in an amount of 6 to 200, preferably 10 to 40 mols per mol of the derivative.

The hydrolyzation in step (b) is conducted at a temperature ranging from 120 to 300° C., preferably 150 to 250° C. for 10 minutes to 48 hours, preferably 30 minutes to 10 hours.

The hydrolyzation may be contemplated in the presence of an organic solvent. In this case, there is used an hydrophobic organic solvent having a boiling point exceeding 100° C., preferably 150° C. such as ethylene glycol, propylene glycol, butane diol, pentane diol, 2-methyl-2,4-pentane diol, hexamethylene glycol, diethylene glycol, triethylene glycol, dipropylene glycol and hexylene glycol. The organic solvent is used in an amount of 1 to 100, preferably 3 to 200 grams per gram of an optical active alkoxybenzonitrile.

Upon completion of hydrolyzation, the resulting mixture after being precipitated using an acid may be spirited of refined by distillation, recrystallization or extraction or by using a column chromatography thereby obtaining an optical active alkoxy benzoic acid derivative.

For instance, an optical active alkoxy benzoic acid derivative can be recovered from the reaction mixture by adding an acid thereto to be precipitated, followed by filtration of the resulting precipitate. Eligible acids are hydrochloric acid, sulfuric acid and nitric acid among which hydrochloric acid is preferred. Precipitation by acid generally occurs at less than 3.5 pH. Alternatively, the intended product may be extracted from the reaction mixture using an organic solvent such as ethyl acetate, ether, toluene, chloroform or methylene chloride and thereafter water remaining in the organic solvent phase is removed as needed, followed by distilling out the organic solvent.

The recovered intended product is then subjected to recrystallization using methanol, ethanol, isopropanol, acetonitrile, or dimethylformaldehyde and thereafter distillation or is refined using a column chromatography thereby obtaining a highly purified optical active alkoxy benzoic acid derivative.

The invention will be further described by way of the following examples which are provided only for illustrative purposes. The synthesis of each example was conducted in nitrogen atmosphere. Sodium hydride was washed with pentane and dried out before use. Dimethylformamide (DMF) was put in use after being dried with molecular sieves.

EXAMPLE 1

Synthesis of (S)-4-(1-methyllheptyloxy)benzonitrile (S)-2-octanol (4.21 g, 32.3 mmol) was dissolved in 15 ml of DMF and added with sodium hydride (0.96 g, 40 mmol) while cooling with ice. Upon completion of alkoxidation reaction effected by stirring for 5 hours at room temperature, the mixture was added with p-fluorobenzonitrile (4.33 g, 35.8 mmol) while cooling with ice and then reacted for 2 hours and further at room temperature for 8 hours, followed by vacuum-distillation of the solvent. The residue was carefully added with 1N diluted hydrochloric acid and then extracted with ethyl acetate. The mixture after being washed with a saturated aqueous solution of sodium hydrogencarbonate was dried over a saturated solution of sodium chloride and anhydrous magnesium sulfate, followed by removal of the solvent thereby obtaining the intended product (7.40 g, 32.0 mmol, 99%).

The results of 1H-NMR (CDCl3, 400 MHz) at the following chemical shifts are as follows:

7.56(m, 2H)
6.90(m, 2H)
4.42(m, 1H)
1.73(m, 1H)
1.58(m, 1H)
1.31(d, J=5.9Hz, 3H)
1.29(m, 8H)
0.88(m, 3H)

EXAMPLE 2

Synthesis of (S)-4-(1-methylhepyloxy)benzonic acid (S)-4-(1-methylheptyloxy)benzonitrile (7.40 g, 32.0 mmol) of Example 1 was mixed with 10 grams potassium hydroxide, 10 ml water and 50 ml ethylene glycol and then heated on an oil bath at a temperature of 200° C. while being refluxed for 3 hours. The mixture after being cooled was added with 100 ml water, followed by filtration of insolubles. The mixture was acidified with 3N hydrochloric acid and a precipitate thus formed was extracted with use of ethyl acetate. The precipitate was washed with a saturated solution of sodium hydrocarbonate and dried over a solution of sodium chloride and anhydrous magnesium sulfate, followed by removal of the solvent. The residue was recrystallized from 200 ml of acetnitrile thereby obtaining the intended product (5.87 g, 23.4 mmol, 73%).

$[\alpha]_D$+10.2 (c 2.0, EtOH)

The results of 1H-NMR (CDCl3, 400 MHz) at the following chemical shifts are as follows:

12.5(br, 1H)
8.3(m, 2H)

```
6.89(m, 2H)
4.45(m, 1H)
1.75(m, 1H)
1.59(m, 1H)
1.31(d, J=6.2Hz, 3H)
1.29(m, 8H)
0.88(m, 3H)
```

EXAMPLE 3

Synthesis of (R)-4-(1-methylheptyloxy)benzonitrile

The procedure of Example 1 was followed except that (R)-2-octanol was used instead of (S)-2-octanol thereby obtaining (R)-4-(1-methylheptyloxy)benzonitrile (7.35 g, 31.8 mmol, 98%).

The results of 1H-NMR (CDCl3, 400 MHz) at the following chemical shifts are as follows:

```
7.56(m, 2H)
6.90(m, 2H)
4.42(m, 1H)
1.73(m, 1H)
1.58(m, 1H)
1.31(d, J=5.9Hz, 3H)
1.29(m, 8H)
0.88(m, 3H)
```

EXAMPLE 4

Synthesis of (R)-4-(1-methylheptyloxy)benzoic acid

The procedure of Example 2 was followed except that (R)-4-(1-methylheptyloxy)benzonitrile (7.35 g, 31.8 mmol) of Example 3 was used in stead of (S)-4-(1-methylheptyloxy)benzonitrile thereby obtaining (R)-4-(1-methylheptyloxy)benzoic acid (5.64 g, 11.5 mmol, 1.71%).

$[\alpha]_D = -10.9$ (c2.0, EtOH)

The results of 1H-NMR (CDCl3, 400 MHz) at the following chemical shifts are as follows:

```
12.5(br, 1H)
8.03(m, 2H)
6.89(m, 2)
4.45(m, 1H)
1.75(m, 1H)
1.59(m, 1H)
1.31(d, j=6.2Hz, 3H)
1.29(m, 8H)
0.88(m, 3H)
```

EXAMPLE 5

Synthesis of 4-((1S,2R,5R)-menthyloxy)benzonitrile

Sodium hydride (3.0 g, 125 mmol) was dispersed in 50 ml dried DMF and added with (−)-menthol (15.6 g, 100 mmol) with stirring while being cooled with ice. The mixture was cooled with ice for 20 minutes and added with 4-chlorobenzonitrile (15.1 g, 100 mmol) while being cooled with ice after alkoxidation reaction progressed at room temperature for 3 hours. The mixture after being stirred while cooling in an ice bath for 2 hours was reacted for 10 hours after taking out the ice bath. There was observed exothermic heat from the reaction product after approximately 2 hours elapsed since the ice bath was removed. After the reaction, DMF was distilled out in vacuum and the residue was added with ether and then washed with use of a solution of diluted caustic soda, diluted hydrochloric acid, a solution of sodium hydrogencarbonate, water and a solution of saturated sodium chloride in the order mentioned, followed by distilling out the solvent. Vacuum distillation was done at a temperature of 150° C. and pressure of 0.5 mmHG using Kugelloa distilling equipment thereby obtaining the intended product (18.8 g, 73.0 mmol, 73%).

The results of 1H-NMR (CDCl3, 400 MHz) at the following chemical shifts are as follows:

```
7.65(m, J=8.8Hz, 2H)
6.92(m, J=8.8Hz, 2H)
4.11(ddd, J=10.8, 10.8, 4.0Hz, 1H)
2.10(m, 2H)
1.73(m, 2H)
1.54(m, 2H)
1.15–0.93(m, 3H)
0.93(d, J=6.6Hz, 3H)
0.92(d, J=6.8Hz, 3H)
0.74(d, J=6.8Hz, 3H)
```

EXAMPLE 6

Synthesis of 4-((1S,2R,5R)-menthyloxy)benzoic acid 4-((1S,2R,5R)-menthyloxy)benzonitrile (8.24 g, 32 mmol) of Example 5 was mixed with 10 gram potassium hydroxide, 10 ml water and 50 ml ethylene glycol and then heated on an oil bath at a temperature of 200° C. while being refluxed for 3 hours. The mixture after being cooled was added with 100 ml water, followed by filtration of insolubles. The mixture was acidified with 3N hydrochloric acid and a precipitate thus formed was extracted with use of ethyl acetate. The precipitate was washed with a saturated solution of sodium hydrocarbonate and then dried over a solution of sodium chloride and anhydrous magnesium sulfate, followed by removal of the solvent. The residue was recrystallized from 200 ml of acetnitrile thereby obtaining the intended product (6.72 g, 24.3 mmol, 76%).

The results of 1H-NMR (CDCl3, 400 MHz) at the following chemical shifts are as follows:

```
12.3(br, 1H)
8.03(d, J=8.8Hz, 2H)
6.93(d, J=8.8Hz, 2H)
4.15(ddd, J=10.4, 10.4, 4.0Hz, 1H)
2.15(m, 1H)
1.74(m, 2H)
1.55(m, 2H)
1.15–0.90(m, 3H)
0.93(m, 6H)
0.75(d, J=6.8Hz, 3H)
```

EXAMPLE 7

Synthesis of 4((1S,2S,5S)-menthyloxy)benzonitrile

The procedure of Example 5 was followed except that (+)-menthol was used instead of (−)-menthol thereby providing the intended product (21.6 g, 84.0 mmol, 84%).

The results of 1H-NMR (CDCl3, 400 MHz) at the following chemical shifts are as follows:

7.55(m, J=8.8Hz, 2H)
6.92(m, J=8.8Hz, 2H)
4.11(ddd, J=10.8, 10.8, 4.0Hz 1H)
2.10(m, 2H)
1.73(m, 2H)
1.54(m, 2H)
1.15–0.93(m, 3H)
0.93(d, j=6.6Hz, 3H)
0.92(d, J=6.8Hz, 3H)
0.74(d, J=6.8Hz, 3H)

EXAMPLE 8

Synthesis of 4-((1R,2S,5S)-menthyloxy)benzoic acid

The procedure of Example 6 was followed except that 4-((1R,2S,5S)-mentyloxy)benzonitrile was used instead of 4-((1R,2R,5R)-menthyloxy)benzonitrile thereby obtaining the intended product (7.16 g, 25.9 mmol, 81%).

The results of 1H-NMR (CDCl3, 400 MHz) at the following chemical shifts are as follows:

12.3(br, 1H)
8.03(d, J=8.8Hz, 2H)
6.93(d, J=8.8Hz, 2H)
4.15(ddd, J=10.4, 10.4, 4.0Hz, 1H)
2.15(m, 2H)
1.74(m, 2H)
1.15–0.90(m, 2H)
1.55(m, 2H)
0.93(m, 6H)
0.75(d, J=6.8Hz, 3H)

EXAMPLE 9

Synthesis of 4-((S)-1-methylpentyloxy)benzoic acid

Sodium hydride (1.86 g, 78 mmol) was dispersed in 30 ml DMF and added with (S)-2-hexanol (6.81 g, 66.6 mmol) with stirring while cooling with ice. After cooling with ice for another one hour, the mixture was stirred at room temperature for 9 hours and cooled again with ice, followed by adding gradually 4-fluorobenzonitrile (8.88 g, 73.3 mmol). After the reaction was continued at room temperature overnight, the mixture was added with 1 ml water while cooling with ice to inactivate excess sodium hydride, followed by removal of DMF in vacuum. The residue was added with 10 grams potassium hydroxide, 10 ml water and 50 ml ethylene glycol and cooled down at room temperature after being heated at a temperature of 200° C. while being refluxed for 9 hours. A crystalline product was dispersed by adding 200 ml water and thereafter carboxylic acid was liberated by acidifying with 3N hydrochloric acid. The carboxylic acid thus obtained was subjected to extraction with ethyl acetate and then washed with use of a saturated solution of sodium chloride. A coarse crystalline product derived after removal of the solvent was recrystallized from acetnitrile thereby obtaining the intended product (16.1 g, 64.8 mmol, 97%).

The results of 1H-NMR (CDCl3, 400 MHz) at the following chemical shifts are as follows:

13.0(br, 1H)
8.04(d, J=8.8Hz, 2H)
6.91(d, J=8.8Hz, 2H)
4.46(m, 1H)
1.75(m, 1H)
1.59(m, 1H)
1.5–1.2(m, 4H)
1.32(d, j=6.2Hz, 3H)
0.88(t, j=5.1Hz, 3H)

EXAMPLE 10

Synthesis of 4-((S)-1-methylhexyloxy)benzoic acid

The procedure of Example 9 was followed except that (S)-2-hexanol was replaced with (S)-2-heptanol in the same mol thereby providing the intended product (16.1 g, 61.3 mol, 92%).

The results of 1H-NMR (CDCl3, 400 MHz) at the following chemical shifts are as follows:

12.2(br, 1H)
8.04(d, J=8.8Hz, 2H)
6.91(d, J=8.8Hz, 2H)
4.46(m, 1H)
1.75(m, 1H)
1.59(m, 1H)
1.5–1.2(m, 6H)
1.33(d, J=5.9Hz, 3H)
0.90(J=7.0Hz, 3H)

EXAMPLE 11

Synthesis of 4-((S)-4-methylpentyloxy)benzoic acid

The procedure of Example 9 was followed except that p-fluorobenzonitrile was replaced with p-chlorobenzonitrile in the same mol and as a solvent used upon hydrolyzation ethylene glycol was replaced with propylene glycol in the same volume thereby providing the intended product (14.5 g, 58.4 mmol, 77%).

The result of 1H-NMR of the product thus obtained was the same as that of Example 9.

EXAMPLE 12

Synthesis of 4-((S)-1-methylheptyloxy)benzonitrile

The procedure of Example 1 was followed except that p-fluorobenzonitrile was replaced with p-nitrobenzonitrile in the same mol thereby providing the intended product (7.33 g, 31.7 mmol, 98%. The result of 1H-NMR of the product thus obtained was the same as that of Example 1.

EXAMPLE 13

Synthesis of 4,4'-((1S,2S)-cyclohexane-1,2-dioxy)bisbenzonitrile

Sodium hydride (7.1 g, 0.3 mol) was dispersed in 200 ml DMF and added with (1S,2S)-cyclohexane-1,2-diol (11.42 g, 98.3 mmol) while cooling with ice. The mixture after being cooled with ice for another one hour was reacted at room temperature for 2 hours and cooled again, followed by addition of p-fluorobenzonitrile (25 g, 206 mmol). After the reaction was continued overnight, the mixture was added carefully with 5 ml water to inactivate excess sodium hydroxide, followed by distillation of DMF in pressure. The residue was added with 200 ml water and then extracted with ethyl acetate, followed by washing with a saturated solution of sodium chloride thereby obtaining a coarse crystalline product. The crystalline product was then recrystallized from 200 ml isopropanol thereby obtaining the intended product (26.2 g, 82.3 mmol, 84%).

The results of 1H-NMR (CDCl3, 400 MHz) at the following chemical shifts are as follows:

```
7.53(m, J=8.8Hz, 4H)
6.92(m, J=8.8Hz, 4H)
4.44(m, 2H)
2.21(m, 2H)
1.83(m, 2H)
1.60(m, 2H)
1.42(m, 2H)
```

EXAMPLE 14

Synthesis of 4,4'-((1S,2S)-cyclohexane-1,2-dioxy) bisbenzoic acid 4,4'-((1S,2S)-cyclohexane-1,2-dioxy)benzonitrile (26.2 g, 82.3 mmol) was mixed with 25 grams potassium hydroxide, 25 grams water and 200 ml ethylene glycol and then heated on an oil bath at a temperature of 200° C. for 2 hours while refluxing. The mixture after being cooled was added with one liter of water and acidified by addition of 40 ml concentrated hydrochloric acid. A precipitate thus formed after being filtrate was dispersed in one liter of hot water and stirred for one hour, followed by drying in vacuum thereby providing the intended product (24.9 g, 69.9 mmol, 85%).

The results of 1H-NMR (CDCl3, 400 MHz) at the following chemical shifts are as follows:

```
12.6(br, 2H)
7.83(m, J=8.8Hz, 4H)
7.01(m, J=8.8Hz, 4H)
4.61(m, 1H)
2.13(m, 2H)
1.70(m, 2H)
1.47(m, 4H)
```

EXAMPLE 15

Synthesis of 4,4'-((S)-methylethanedioxy) benzonitrile

Sodium hydride (4.32 g, 180 mmol) was dispersed in 80 ml DMF and added with 2-(S)-propanediol (5.29 g, 69.5 mmol) while being cooled with ice. After being cooled with ice for another one hour, the mixture was stirred at room temperature for 2 hours and added with 4-chlorobenzonitrile (17.6 g, 128 mmol) at room temperature. The mixture was then reacted at room temperature for 5 hours and further at a temperature of 70° C. for 3 hours. After completion of the reaction, the reaction mixture was added carefully with 5 ml water to inactivate excess sodium hydride, followed by distillation of DMF in pressure. A precipitate resulted from addition of 200 ml of water to the residue was filtrated and thereafter recrystallized from 100 ml ethanol thereby obtaining the intended product (14.5 g, 52.1 mmol, 75%).

The results of 1H-NMR (CDCl3, 270 MHz) at the following chemical shifts are as follows:

```
7.59(m, 4H)
6.99(m, J=9.2Hz, 2H)
6.94(m, J=9.2Hz, 2H)
4.86(dddd, J=12.7, 6.2, 6.2, 4.3Hz, 1H)
4.20(d, J=6.2Hz, AB, J=10.0Hz, Δn=25.2Hz, 1H)
4.11(d, J=4.3Hz, AB, J=10.0Hz, Δn=25.2Hz, 1H)
1.47(d, J=6.5Hz, 3H)
```

EXAMPLE 16

Synthesis of 4,4'-((S)-methylethanedioxy)bisbenzoic acid 4,4'-((S)-methylethanedioxy)bisbenzonitrile of Example 15 was mixed with 5 grams of potassium hydroxide, 5 grams of water and 40 ml ethylene glycol and then heated on an oil bath at a temperature of 200° C. while refluxing for 3 hours. After cooling the mixture, a crystalline product was precipitated therein and then added with 100 ml methanol, followed by filtration of the crystalline product. The crystalline product was dissolved in 150 ml water and acidified by adding 3N hydrochloric acid. A precipitate thus formed was filtrated and washed with water, followed by drying in vacuum thereby obtaining the intended product (7.83 g, 24.8 mmol, 69%).

The results of 1H-NMR (DMSO, 400 MHz) at the following chemical shifts are as follows:

```
12.6(br, 2H)
7.88(d, J=8.8Hz, 4H)
7.06(d, J=8.8Hz, 2H)
7.04(d, J=8.8Hz, 2H)
4.99(m, 1H)
4.24(m, 2H)
1.37(d, J=6.4Hz, 3H)
```

EXAMPLE 17

Synthesis of 4,4'-((R)-1-methylpropanedioxy) bisbenzonitrile

Sodium hydride (3.18 g, 133 mmol) was dispersed in 100 ml DMF and added with 1,3-(R)-butanediol (5.03 g, 55.8 mmol) while being cooled with ice. The mixture after being cooled with ice for another one hour was stirred at room temperature for 2 hours and then added with 4-chlorobenzonitrile (16.8 g, 122 mmol) at room temperature, followed by being reacted for 20 hours. After completion of the reaction, the reaction mixture was carefully added with 5 ml water to inactivate excess sodium hydride, followed by distilling out DMF in vacuum. The resulting mixture after being added with 200 ml of water was subjected to processes of extraction of an organic matter with ethyl acetate, washing with a solution of saturated sodium chloride and distillation of the solvent, followed by distillation of the oily residue thus obtained using Kugelloa distilling equipment at a temperature of 275° C. and a pressure of 0.5 mmHg thereby obtaining the intended product (13.3 g, 45.4 mmol, 81%).

The results of 1H-NMR (CDCl3, 270 MHz) at the following chemical shifts are as follows:

7.56(m, 4H)
6.93(m, 4H)
4.74(m, 1H)
4.14(m, 2H)
2.18(m, 2H)
1.40(d, J=5.9Hz, 3H)

EXAMPLE 18

Synthesis of 4,4'-((R)-1-methylpropanedioxy)bisbenzoic acid 4,4'-((R)-1-methylpropanedioxy)bisbenzonitrile (11.6 g, 39.6 mmol) of Example 17 was mixed with the 6 grams potassium hydroxide, 6 grams of water and 60 ml ethylene glycol and thereafter heated on an oil bath at a temperature of 200° C. while being refluxed for 8 hours. The reaction mixture after being cooled with ice was added with 300 ml isopropanol followed by centrifuge separation of a precipitate thus obtained. The precipitate was dissolved in 150 ml water and then acidified with 3N hydrochloric acid. A precipitate thus obtained was subjected to centrifuge separation and then washed with water, followed by drying in vacuum thereby obtaining the intended product (11.0 g, 33.3 mmol, 84%).

The results of 1H-NMR (DMSO, 400 MHz) at the following chemical shifts are as follows:

12.6(br, 2H)
7.86(m, 4H)
7.02(m, 4H)
4.78(m, 1H)
4.17(m, 2H)
2.11(m, 2H)
1.34(d, J=6.4Hz, 3H)

EXAMPLE 19

Synthesis of 4,4'-((S)-2-methylbutanedioxy)bisbenzonitrile

Sodium hydride (2.88 g, 120 mmol) was dispersed in 50 ml DMF and then added with (S)-2-methyl-1,4-butanediol (5.21 g, 50.0 mmol) while being iced with ice. The reaction mixture after being cooled with ice for another one hour was stirred at room temperature for 2 hours and then added with 4-chlorobenzonitrile (15.3 g, 120 mmol), followed by reaction for 20 hours. After completion of the reaction, the reaction mixture was added carefully with 5 ml water to inactivate excess sodium hydride, followed by vacuum-distillation of DMF. After addition of 200 ml water, a precipitate thus obtained was filtrated and recrystallized from 100 ml ethanol thereby providing the intended product (12.5 g, 40.8 mmol, 82%).

The results of 1H-NMR (CDCl3, 400 MHz) at the following chemical shifts are as follows:

7.58(m, J=8.4Hz, 4H)
6.93(m, 4H)
4.12(m, 2H)
3.91(d, J=6.0Hz, 2H)
2.27(m, 1H)
2.08(m, 1H)
1.79(m, 1H)
1.12(d, J=6.8Hz, 3H)

EXAMPLE 20

Synthesis of 4,4'-((S)-2-methylbutanedioxy)bisbenzoic acid 4,4'-((S)-2-methylbutanedioxy)bisbenzonitrile (12.1 g, 39.5 mmol) of Example 19 was mixed with 7.5 grams potassium hydroxide, 7.5 grams water and 75 ml ethylene glycol and then heated on an oil bath at a temperature of 200° C. for 3 hours while being refluxed. The reaction after being cooled was added with 500 ml water and then acidified with use of 3N hydrochloric acid. A precipitate thus derived was filtrated and recrystallized from ethanol thereby providing the intended product (13.2 g, 38.4 mmol, 97%).

The results of 1H-NMR (DMSO, 270 MHz) at the following chemical shifts are as follows:

12.6(br, 2H)
7.88(d, J=8.8Hz, 4H)
7.01(d, J=9.1Hz, 4H)
4.16(m, 2H)
3.99(d, J=5.9Hz, AB, J=9.5Hz, Δn=17.1Hz, 1H)
3.93(d, J=6.2Hz, AB, J=9.5Hz, Δn=17.1Hz, 1H)
2.16(m, 1H)
1.96(m, 1H)
1.72(m, 1H)
1.06(d, J=6.6Hz, 3H)

EXAMPLE 21

Synthesis of 4-((S)-4-methylhexyloxy)benzoic acid

The procedure of Example 9 was followed except that (S)-2-hexanol was replaced with (S)-4-methylhexanol in the same mol thereby obtaining the intended product (14.8 g, 62.6 mmol, 94%).

The results of 1H-NMR (CDCl3, 270 MHz) at the following chemical shifts are as follows:

11.8(br,1 H)
8.06(m, J=8.8Hz, 2H)
6.93(m, J=8.8Hz, 2H)
4.01(t, J=6.4Hz, 2H)
1.81(m, 2H)
1.51–1.15(m, 5H)
0.91(d, J=6.1Hz, 3H)
0.89(t, J=7.3Hz, 3H)

EXAMPLE 22

Synthesis of 4-((S)-1-methylpentyloxy)benzoic acid

The procedure of Example 9 was followed that potassium hydroxide was replaced with sodium hydroxide in the same weight thereby obtaining the intended product (15.6 g, 62.8 mmol, 94%).

The result of 1H-NMR of this example was same as that of Example 9.

The process according to the invention can produce an optical active alkoxybenzonitrile derivative and an optical active alkoxy benzoic acid derived from hydrolyzation of the alkoxybenzonitrile derivative in a simple manner in which an optical active alcohol can be reacted with benzonitrile without converting the alcohol to tosylate or halide.

What is claimed is:

1. A process for producing an optically active alkoxybenzonitrile derivative wherein a benzonitrile derivative and an optically active alcohol are subjected to a condensation reaction in the presence of a base, and wherein said benzonitrile derivative is represented by the formula (I):

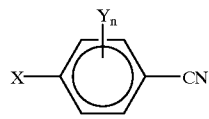
(I)

wherein X is an atom of fluorine or chlorine or a nitro group, Y is a $C_1$–$C_{10}$ alkyl group and n is an integer of 1–4.

2. A process for producing an optically active alkoxy benzoic acid derivative wherein a benzonitrile derivative and an optically active alcohol are subjected to a condensation reaction in the presence of a base and the resulting reaction product is subjected to hydrolyzation, wherein said benzonitrile derivative is represented by the formula (I):

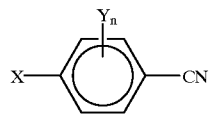
(I)

wherein X is an atom of fluorine or chlorine or a nitro group, Y is a $C_1$–$C_{10}$ alkyl group and n is an integer of 1–4.

3. A process according to claim 1 wherein said benzonitrile derivative of said formula (I) is selected from the group consisting of 4-fluorobenzonitrile, 4-chlorobenzonitrile and 4-nitrobenzonitrile.

4. A process according to claim 1 wherein said optical active alcohol is selected from the group consisting of a $C_4$–$C_{30}$ monoalcohol, a $C_3$–$C_{30}$ diol and a $C_4$–$C_{30}$ triol.

5. A process according to claim 1 wherein said base is selected from the group consisting of sodium hydride, metallic sodium and potassium t-butyrate.

6. A process according to claim 1 wherein said condensation reaction is conducted using a reactive solvent selected from the group consisting of dimethylformaldehyde, dimethylacetamide, tetrahydrofuran and pyridine.

7. A process according to claim 2 wherein said hydrolyzation is effected at a temperature of 120–300° C. for 10 minutes to 48 hours.

8. A process according to claim 2 wherein said hydrolyzation is conducted in the presence of an organic solvent selected from the group consisting of ethylene glycol, propylene glycol, butane diol, pentane diol, 2-methyl-2,4-pentanediol, hexamethylene glycol, diethylene glycol, triethylene glycol, dipropylene glycol and hexylene glycol.

* * * * *